United States Patent [19]

Lewis et al.

[11] Patent Number: 5,571,401
[45] Date of Patent: Nov. 5, 1996

[54] SENSOR ARRAYS FOR DETECTING ANALYTES IN FLUIDS

[75] Inventors: Nathan S. Lewis, La Canada, Calif.; Michael S. Freund, Allentown, Pa.

[73] Assignee: California Institute of Technology, Pasadena, Calif.

[21] Appl. No.: 410,809

[22] Filed: Mar. 27, 1995

[51] Int. Cl.$^6$ .................................................. G01N 27/26
[52] U.S. Cl. .................. 205/787; 204/418; 204/415; 204/406; 205/775; 205/782.5; 422/68.1; 422/69; 422/82.01; 422/82.02; 422/83; 422/98; 436/150
[58] Field of Search ........................... 204/418, 415, 204/153.1, 406, 153.17, 153.2; 422/98, 69, 83, 68.1, 82.01, 82.02; 436/150

[56] References Cited

U.S. PATENT DOCUMENTS

| | | | |
|---|---|---|---|
| 4,759,210 | 7/1988 | Wohltjen | 422/88 |
| 4,907,441 | 3/1990 | Shurmer | 73/23 |
| 4,992,244 | 2/1991 | Grate | 422/98 |
| 5,045,285 | 9/1991 | Kolesar, Jr. | 422/98 |
| 5,120,421 | 6/1992 | Glass et al. | 204/406 |

OTHER PUBLICATIONS

Lundstrom, I., et al., "Artificial 'olfactory' images from a chemical sensor using a light-pulse technique", *Nature*, 352:47–50 (1991). No month available.

Shurmer, H. V., et al., "Odour discrimination with an electronic nose", *Sensors and Actuators B*, 8:1–11 (1992). No month available.

Gardner, J. W., et al., "Integrated Tin Oxide Odour Sensors", *Sensors and Actuators B*, 4:117–121 (1991). No month available.

Gardner, J. W. et al., "Application of an electronic nose to the discrimination of coffees", *Sensors and Actuators B*, 6:71–75 (1992). No month available.

Grate, J. W., et al., "Solubility interactions and the design of chemically selective sorbent coatings for chemical sensors and arrays", *Sensors and Actuators B*, 3:85–111 (1991). No month available.

Grate, J. W., et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition", *Anal. Chem.*, 65:1868–1881 (1993). No month available.

Stetter, J. R., et al., "Quality classification of grain using a sensor array and pattern recognition", *Analytica Chimica Acta*, 284:1–11 (1993). No month available.

(List continued on next page.)

*Primary Examiner*—Bruce F. Bell
*Attorney, Agent, or Firm*—Richard F. Trecartin; Flehr, Hohbach, Test, Albritton & Herbert

[57] ABSTRACT

Chemical sensors for detecting analytes in fluids comprise first and second conductive elements (e.g. electrical leads) electrically coupled to and separated by a chemically sensitive resistor which provides an electrical path between the conductive elements. The resistor comprises a plurality of alternating nonconductive regions (comprising a nonconductive organic polymer) and conductive regions (comprising a conductive material) transverse to the electrical path. The resistor provides a difference in resistance between the conductive elements when contacted with a fluid comprising a chemical analyte at a first concentration, than when contacted with a fluid comprising the chemical analyte at a second different concentration. Arrays of such sensors are constructed with at least two sensors having different chemically sensitive resistors providing dissimilar such differences in resistance. Variability in chemical sensitivity from sensor to sensor is provided by qualitatively or quantitatively varying the composition of the conductive and/or nonconductive regions. An electronic nose for detecting an analyte in a fluid may be constructed by using such arrays in conjunction with an electrical measuring device electrically connected to the conductive elements of each sensor.

10 Claims, 8 Drawing Sheets

OTHER PUBLICATIONS

Pearce, T. C., et al., "Electronic Nose for Monitoring the Flavour of Beers", *Analyst*, 118:371–377 (1993). No month available.

Shurmer, H. V., et al., "Integrated Arrays of Gas Sensors Using Conducting Polymers with Molecular Sieves", *Sensors and Actuators B*, 4:29–33 (1991). No month available.

Topart, P., et al., "Characterization of the Interaction between Poly(pyrrole) Films and Methanol Vapor", *J. Phys. Chem.*, 96:7824–7830 (1992). No month available.

Charlesworth, J. M., et al., "Mechanistic Studies on the Interactions between Poly(pyrrole) and Organic Vapors", *J. Phys. Chem.*, 97:5418–5423 (1993). No month available.

Gardner, J. W., et al., "Design of conducting Polymer Gas Sensors: Modelling and Experiment", *Synthetic Metals*, 55–57:3665–3670 (1993). No month available.

Gardner, J. W., et al., "Detection of vapours and odours from a multisensor array using pattern–recognition techniques Part 2. Artificial neural networks", *Sensors and Actuators B*, 9:9–15 (1992). No month available.

Gardner, J. W., et al., "Detection of Vapours and Odours from a Multisensor Array Using Pattern Recognition Part 1. Principal Component and Cluster Analysis", *Sensors and Actuators B*, 4:109–115 (1991). No month available.

Bartlett, P. N., et al., "Electrochemical Deposition of Conducting Polymers onto Electronic Substrates for Sensor Applications", *Sensors and Actuators*, A21–A23:911–914 (1990). No month available.

Gardner, J. W., et al., "A multisensor system for beer flavour monitoring using an array of conducting polymers and predictive classifiers", *Sensors and Actuators B*, 18–19:240–243 (1994). No month available.

Gardner, J. W., et al., "A brief history of electronic noses*", *Sensors and Actuators B*, 18–19:211–220 (1994). No month available.

Zaromb, S., et al., "Theoretical Basis for Identification and Measurement of Air Contaminants Using An Array of Sensors Having Partly Overlapping Selectivities", *Sensors and Actuators*, 6:225–243 (1984). No month available.

SENSOR ARRAYS FOR DETECTING ANALYTES IN FLUIDS

The research carried out in the subject application was supported in part by grants from the National Science Foundation (CHE 9202583) was made during the performance of work under a NASA contract, and is subject to the provisions of Public Law 96-517 (35 USC 202). The government may have rights in any patent issuing on this application.

INTRODUCTION

1. Field of the Invention

The field of the invention is electrical sensors for detecting analytes in fluids.

2. Background

There is considerable interest in developing sensors that act as analogs of the mammalian olfactory system (references 1–2). This system is thought to utilize probabilistic repertoires of many different receptors to recognize a single odorant (references 3–4). In such a configuration, the burden of recognition is not on highly specific receptors, as in the traditional "lock-and-key" molecular recognition approach to chemical sensing, but lies instead on the distributed pattern processing of the olfactory bulb and the brain (references 5–6).

Prior attempts to produce a broadly responsive sensor array have exploited heated metal oxide thin film resistors (references 7–9), polymer sorption layers on the surfaces of acoustic wave resonators (references 10–11), arrays of electrochemical detectors (12–14), or conductive polymers (references 15–16). Arrays of metal oxide thin film resistors, typically based on $SnO_2$ films that have been coated with various catalysts, yield distinct, diagnostic responses for several vapors (references 7–9). However, due to the lack of understanding of catalyst function, $SnO_2$ arrays do not allow deliberate chemical control of the response of elements in the arrays nor reproducibility of response from array to array. Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHz Rayleigh wave in the crystal (references 10–11). Attempts have been made to construct sensors with conducting polymer elements that have been grown electrochemically through nominally identical polymer films and coatings (references 15–18).

It is an object herein to provide a broadly responsive analyte detection sensor array based on a variety of "chemiresistor" elements. Such elements are simply prepared and are readily modified chemically to respond to a broad range of analytes. In addition, these sensors yield a rapid, low power, dc electrical signal in response to the fluid of interest, and their signals are readily integrated with software or hardware-based neural networks for purposes of analyte identification.

Relevant Literature

Pearce et al (1993) Analyst 118, 371–377 and Gardner et al (1994) Sensors and Actuators B, 18–19, 240–243 describe polypyrrole-based sensor arrays for monitoring beer flavor. Shurmer (1990) U.S. Pat. No. 4,907,441 describes general sensor arrays with particular electrical circuitry.

SUMMARY OF THE INVENTION

The invention provides methods, apparatuses and expert systems for detecting analytes in fluids. The apparatuses include a chemical sensor comprising first and second conductive elements (e.g. electrical leads) electrically coupled to a chemically sensitive resistor which provides an electrical path between the conductive elements. The resistor comprises a plurality of alternating nonconductive regions (comprising a nonconductive organic polymer) and conductive regions (comprising a conductive material). The electrical path between the first and second conductive elements is transverse to (i.e. passes through) said plurality of alternating nonconductive and conductive regions. In use, the resistor provides a difference in resistance between the conductive elements when contacted with a fluid comprising a chemical analyte at a first concentration, than when contacted with a fluid comprising the chemical analyte at a second different concentration.

The electrical path through any given nonconductive region is typically on the order of 100 angstroms in length, providing a resistance of on the order of 100 m$\Omega$ across the region. Variability in chemical sensitivity from sensor to sensor is conveniently provided by qualitatively or quantitatively varying the composition of the conductive and/or nonconductive regions. For example, in one embodiment, the conductive material in each resistor is held constant (e.g. the same conductive material such as polypyrrole) while the nonconductive organic polymer varies between resistors (e.g. different plastics such as polystyrene).

Arrays of such sensors are constructed with at least two sensors having different chemically sensitive resistors providing dissimilar differences in resistance. An electronic nose for detecting an analyte in a fluid may be constructed by using such arrays in conjunction with an electrical measuring device electrically connected to the conductive elements of each sensor. Such electronic noses may incorporate a variety of additional components including means for monitoring the temporal response of each sensor, assembling and analyzing sensor data to determine analyte identity, etc. Methods of making and using the disclosed sensors, arrays and electronic noses are also provided.

BRIEF DESCRIPTION OF THE FIGURES

FIG. 4(A) Schematic of a sensor array showing an enlargement of one of the modified ceramic capacitors used as sensing elements. The response patterns generated by the sensor array described in Table 3 are displayed for.

FIG. 6A shows data represented in the first three principle component pc1, pc2 and pc3, while FIG. 6B shows the data when represented in pc1, pc2, and pc4. A higher degree of discrimination between some solvents could be obtained by considering the fourth principle component as illustrated by larger separations between chloroform, tetrahydrofuran, and isopropyl alcohol in FIG. 6B.

DETAILED DESCRIPTION OF THE INVENTION

The invention provides sensor arrays for detecting an analyte in a fluid for use in conjunction with an electrical measuring apparatus. These arrays comprise a plurality of compositionally different chemical sensors. Each sensor comprises at least first and second conductive leads electrically coupled to and separated by a chemically sensitive resistor. The leads may be any convenient conductive material, usually a metal, and may be interdigitized to maximize signal-to-noise strength.

The resistor comprises a plurality of alternating nonconductive and conductive regions transverse to the electrical path between the conductive leads. Generally, the resistors are fabricated by blending a conductive material with a nonconductive organic polymer such that the electrically conductive path between the leads coupled to the resistor is interrupted by gaps of non-conductive organic polymer material. For example, in a colloid, suspension or dispersion of particulate conductive material in a matrix of nonconductive organic polymer material, the matrix regions separating the particles provide the gaps. The nonconductive gaps range in path length from about 10 to 1,000 angstroms, usually on the order of 100 angstroms providing individual resistance of about 10 to 1,000 mΩ, usually on the order of 100 mΩ, across each gap. The path length and resistance of a given gap is not constant but rather is believed to change as the nonconductive organic polymer of the region absorbs, adsorbs or imbibes an analyte. Accordingly the dynamic aggregate resistance provided by these gaps in a given resistor is a function of analyte permeation of the nonconductive regions. In some embodiments, the conductive material may also contribute to the dynamic aggregate resistance as a function of analyte permeation (e.g. when the conductive material is a conductive organic polymer such as polyprryole).

A wide variety of conductive materials and nonconductive organic polymer materials can be used. Table 1 provides exemplary conductive materials for use in resistor fabrication; mixtures, such as of those listed, may also be used. Table 2 provides exemplary nonconductive organic polymer materials; blends and copolymers, such as of the polymers listed here, may also be used. Combinations, concentrations, blend stoichiometries, percolation thresholds, etc. are readily determined empirically by fabricating and screening prototype resistors (chemiresistors) as described below.

| Major Class | Examples |
|---|---|
| Organic Conductors | conducting polymers (poly(anilines), poly(thiophenes), poly(pyrroles), poly(acetylenes), etc.)), carbonaceous materials (carbon blacks, graphite, coke, $C_{60}$, etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, InP, $MoS_2$, $TiO_2$, etc.), conductive metal oxides ($In_2O_3$, $SnO_2$, $Na_xPt_3O_4$, etc.), superconductors ($YBa_2Cu_3O_7$, $Tl_2Ba_2Ca_2Cu_3O_{10}$, etc.), etc. |
| Mixed inorganic/organic Conductor | Tetracyanoplatinate complexes, Iridium halocarbonyl complexes, stacked macrocyclic complexes, etc. |

TABLE 2

| Major Class | Examples |
|---|---|
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryienes), etc. |
| Main-chain acyclic heteroatom polymers | poly(oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), etc. |
| Main-chain heterocyclic polymers | poly(furan tetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), carbohydrates, etc. |

The chemiresistors can be fabricated by many techniques such as, but not limited to, solution casting, suspension casting, and mechanical mixing. In general, solution cast routes are advantageous because they provide homogeneous structures and ease of processing. With solution cast routes, resistor elements may be easily fabricated by spin, spray or dip coating. Since all elements of the resistor must be soluble, however, solution cast routes are somewhat limited in their applicability. Suspension casting still provides the possibility of spin, spray or dip coating but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the conducting and non-conducting media or their reaction precursors are soluble in a common solvent, the chemiresistors can be fabricated by solution casting. The oxidation of pyrrole by phosphomolybdic acid presented herein represents such a system. In this reaction, the phosphomolybdic acid and pyrrole are dissolved in tetrahydrofuran (THF) and polymerization occurs upon solvent evaporation. This allows for THF soluble non-conductive polymers to be dissolved into this reaction mixture thereby allowing the blend to be formed in a single step upon solvent evaporation. The choice of non-conductive polymers in this route is, of course, limited to those that are soluble in the reaction media. For the poly(pyrrole) case described above, preliminary reactions were performed in THF, but this reaction should be generalizable to other non-aqueous solvent such as acetonitrile or ether. A variety of permutations on this scheme are possible for other conducting polymers. Some of these are listed below. Certain conducting polymers, such as substituted poly(cyclooctatetraenes), are soluble in their undoped, non-conducting state in solvents such as THF or acetonitrile. Consequently, the blends between the undoped polymer and plasticizing polymer can be formed from solution casting. After which, the doping procedure (exposure to $I_2$ vapor, for instance) can be performed on the blend to render the substituted poly-(cyclooctatetraene) conductive. Again, the choice of non-conductive polymers is limited to those that are soluble in the solvents that the undoped conducting polymer is soluble in and to those stable to the doping reaction. Certain conducting polymers can also be synthesized via a soluble precursor polymer. In these cases, blends between the precursor polymer and the non-conducting polymer can first be formed followed by chemical reaction to convert the precursor polymer into the desired conducting polymer. For instance poly(p-phenylene vinylene) can be synthesized through a soluble sulfonium precursor. Blends between this sulfonium precursor and the non-conductive polymer can be formed by solution casting. After which, the blend can be subjected to thermal treatment under vacuum to convert the sulfonium precursor to the desired poly(p-phenylene vinylene).

In suspension casting, one or more of the components of the resistor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the non-conductive polymer is dissolved in an appropriate solvent (such as THF, acetonitrile, water, etc.). Colloidal silver is then suspended in this solution and the resulting mixture is used to dip coat electrodes.

Mechanical mixing is suitable for all of the conductive/non-conductive combinations possible. In this technique, the materials are physically mixed in a ball-mill or other mixing device. For instance, carbon black: non-conductive polymer composites are readily made by ball-milling. When the non-conductive polymer can be melted or significantly softened without decomposition, mechanical mixing at elevated temperature can improve the mixing process. Alternatively, composite fabrication can sometimes be improved by several sequential heat and mix steps.

Once fabricated, the individual elements can be optimized for a particular application by varying their chemical make up and morphologies. The chemical nature of the resistors determines to which analytes they will respond and their ability to distinguish different analytes. The relative ratio of conductive to insulating components determines the magnitude of the response since the resistance of the elements becomes more sensitive to sorbed molecules as the percolation threshold is approached. The film morphology is also important in determining response characteristics. For instance, thin films respond more quickly to analytes than do thick ones. Hence, with an empirical catalogue of information on chemically diverse sensors made with varying ratios of insulating to conducting components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques:chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high transition metal (Tm) polymers), the incorporation of the resistor elements into supporting matrices such as clays or polymer networks (forming the resistor blends within poly-(methylmethacrylate) networks or within the lamellae of montmorillonite, for instance), etc. In another embodiment, the resistor is deposited as a surface layer on a solid matrix which provides means for supporting the leads. Typically, the matrix is a chemically inert, non-conductive substrate such as a glass or ceramic.

Sensor arrays particularly well-suited to scaled up production are fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip which contains the circuitry for analogue signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different polymers in solution which can be deposited are used. A sensor array of a million distinct elements only requires a 1 cm×1 cm sized chip employing lithography at the 10 µm feature level, which is within the capacity of conventional commercial processing and deposition methods. This technology permits the production of sensitive, small-sized, stand-alone chemical sensors.

Preferred sensor arrays have a predetermined inter-sensor variation in the structure or composition of the nonconductive organic polymer regions. The variation may be quantitative and/or qualitative. For example, the concentration of the nonconductive organic polymer in the blend can be varied across sensors. Alternatively, a variety of different organic polymers may be used in different sensors. An electronic nose for detecting an analyte in a fluid is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis. Typically such a nose comprises at least ten, usually at least 100, and often at least 1000 different sensors though with mass deposition fabrication techniques described herein or otherwise known in the art, arrays of on the order of at least $10^6$ sensors are readily produced.

In operation, each resistor provides a first electrical resistance between its conductive leads when the resistor is contacted with a first fluid comprising a chemical analyte at a first concentration, and a second electrical resistance between its conductive leads when the resistor is contacted with a second fluid comprising the same chemical analyte at a second different concentration. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors which respond differently to a change in an analyte concentration, i.e. the difference between the first and second electrical resistance of one sensor is different from the difference between the first second electrical resistance of another sensor.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analyte may then be characterized or identified using response pattern comparison and recognition algorithms. Accordingly, analyte detection systems comprising sensor arrays, an electrical measuring devise for detecting resistance across each chemiresistor, a computer, a data structure of sensor array response profiles, and a comparison algorithm are provided. In another embodiment, the electrical measuring device is an integrated cicuit comprising neural network-based hardware and a digital-analog converter (DAC) multiplexed to each sensor, or a plurality of DACs, each connected to different sensor(s).

A wide variety of analytes and fluids may be analyzed by the disclosed sensors, arrays and noses so long as the subject analyte is capable generating a differential response across a plurality of sensors of the array. Analyte applications include broad ranges of chemical classes such as organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g. halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, etc.

The general method for using the disclosed sensors, arrays and electronic noses, for detecting the presence of an analyte in a fluid involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration.

The following examples are offered by way of illustration and not by way of limitation.

EXAMPLES

Polymer Synthesis. Poly(pyrrole) films used for conductivity, electrochemical, and optical measurements were prepared by injecting equal volumes of $N_2$-purged solutions of pyrrole (1.50 mmoles in 4.0 ml dry tetrahydrofuran) and phosphomolybdic acid (0.75 mmoles in 4.0 ml tetrahydrofuran) into a $N_2$-purged test tube. Once the two solutions were mixed, the yellow phosphomolybdic acid solution turned dark green, with no observable precipitation for several hours. This solution was used for film preparation within an hour of mixing.

Sensor Fabrication. Plasticized poly(pyrrole) sensors were made by mixing two solutions, one of which contained 0.29 mmoles pyrrole in 5.0 ml tetrahydrofuran, with the other containing 0.25 mmoles phosphomolybdic acid and 30 mg of plasticizer in 5.0 ml of tetrahydrofuran. The mixture of these two solutions resulted in a w:w ratio of pyrrole to plasticizer of 2:3. An inexpensive, quick method for crating the chemiresistor array elements was accomplished by effecting a cross sectional cut through commercial 22 nF ceramic capacitors (Kemet Electronics Corporation). Mechanical slices through these capacitors revealed a series of interdigitated metal lines (25 % Ag:75 % Pt), separated by 15 μm, that could be readily coated with conducting polymer. The monomer—plasticizer—oxidant solutions were then used to dip coat interdigitated electrodes in order to provide a robust electrical contact to the polymerized organic films. After polymerization was complete, the film was insoluble and was rinsed with solvent (tetrahydrofuran or methanol) to remove residual phosphomolybdic acid and unreacted monomer. The sensors were then connected to a commercial bus strip, with the resistances of the various "chemiresistor" elements readily monitored by use of a multiplexing digital ohmmeter.

Instrumentation. Optical spectra were obtained on a Hewlett Packard 8452A spectrophotometer, interfaced to an IBM XT. Electrochemical experiments were performed using a Princeton Applied Research Inc. 173 potentiostat/175 universal programmer. All electrochemical experiments were performed with a Pt flag auxiliary and a saturated calomel reference electrode (SCE). Spin-coating was performed on a Headway Research Inc. photoresist spin coater. Film thicknesses were determined with a Dektak Model 3030 profilometer. Conductivity measurements were performed with an osmium-tipped four point probe (Alessi Instruments Inc., tip spacing=0.050", tip radii=0.010"). Transient resistance measurements were made with a conventional multimeter (Fluke Inc., "Hydra Data Logger" Meter).

Principle Component Analysis and Multi-linear Least Square Fits. A data set obtained from a single exposure of the array to an odorant produced a set of descriptors (i.e. resistances), di. The data obtained from multiple exposures thus produced a data matrix D where each row, designated by j, consisted of n descriptors describing a single member of the data set (i.e. a single exposure to an odor). Since the baseline resistance and the relative changes in resistance varied among sensor,s the data matrix was autoscaled before further processing (19). In this preprocessing technique, all the data associated with a single descriptor (i.e. a column in the data matrix) were centered around zero with unit standard deviation $$d'_{ij}=(d_{ij}-\bar{d}_i)/\sigma_i \tag{1}$$

where $\bar{d}_i$ is the mean value for descriptor i and $\sigma_i$ is the corresponding standard deviation.

Principle component analysis (reference 19) was performed to determine linear combinations of the data such that the maximum variance [defined as the square of the standard deviation] between the members of the data set was obtained in n mutually orthogonal dimensions. The linear combinations of the data resulted in the largest variance [or separation] between the members of the data set in the first principle component (pc1) and produced decreasing magnitudes of variance from the second to the $n^{th}$ principle component (pc2–pcn). The coefficients required to transform the autoscaled data into principle component space (by linear combination) were determined by multiplying the data matrix, D, by its transpose, $D^T$ (i.e. diagnolizing the matrix)(reference 19)

$$R=D^T \cdot D \tag{2}$$

This operation produced the correlation matrix, R whose diagonal elements were unity and whose off-diagonal elements were the correlation coefficients of the data. The total variance in the data was thus given by the sum of the diagonal elements in R. The n eigenvalues, and the corresponding n eigenvectors, were then determined for R. Each eigenvector contained a set of n coefficients which were used to transform the data by linear combination into one of its n principle components. The corresponding eigenvalue yielded the fraction of the total variance that was contained in that principle component. This operation produced a principle component matrix, P, which had the same dimensions as the original data matrix. Under these conditions, each row of the matrix P was still associated with a particular odor and each column was associated with a particular principle component.

Since the values in the principle component space had no physical meaning, it was useful to express the results of the principle component analysis in terms of physical parameters such as partial pressure and mole fraction. This was achieved via a multi-linear least square fit between the principle component values and the corresponding parameter of interest. A multi-linear least square fit resulted in a linear combination of the principle components which yielded the best fit to the corresponding parameter value. Fits were achieved by appending a column with each entry being unity to the principle component matrix P, with each row, j, corresponding to a different parameter value (e.g. partial pressure), $v_j$, contained in vector V. The coefficients for the best multi-linear fit between the principle components and parameter of interest were obtained by the following matrix operation

$$C=(P^T \cdot P)^{-1} \cdot P^T \cdot V \tag{3}$$

where C was a vector containing the coefficients for the linear combination.

A key to our ability to fabricate chemically diverse sensing elements was the preparation of processable, air stable films of electrically conducting organic polymers. This was achieved through the controlled chemical oxidation of pyrrole (PY) using phosphomolybdic acid ($H_3PMo_{12}O_{40}$) (20 in tetrahydrofuran:

$$PY \rightarrow PY^+ + e^- \tag{4}$$

$$2PY^+ \rightarrow PY_2 + 2H^+ \tag{5}$$

$$H_3PMo_{12}O_{40} + 2e^- 2H^+ \rightarrow H_5PMo_{12}O_{40} \tag{6}$$

The redox-driven or electrochemically-induced polymerization of pyrrole has been explored previously, but this process typically yields insoluble, intractable deposits of poly(pyrrole) as the product (reference 21 ). Our approach was to use low concentrations of the $H_3PMo_{12}O_{40}$ oxidant ($E°=+0.36$ V vs. SCE) (reference 20). Since the electrochemical potential of $PY^+/PY$ is more positive ($E°=+1.30$ V vs. SCE) (reference 22) than that of $H_3PMo_{12}O_{40}/H_5PMo_{12}O_{40}$, the equilibrium concentration of $PY^+$, and thus the rate of polymerization, was relatively low in dilute solutions (0.19M PY, 0.09M $H_3PMo_{12}O_{40}$). However, it has been shown that the oxidation potential of pyrrole oligomers decreases from +1.20 V to +0.55 to +0.26 V vs. SCE as the number of units increase from one to two to three, and that the oxidation potential of bulk poly(pyrrole) occurs at −0.10 V vs. SCE (reference 23). As a result, oxidation of pyrrole trimers by phosphomolybdic acid is expected to be thermodynamically favorable. This allowed processing of the monomer-oxidant solution (i.e. spin coating, dip coating, introduction of plasticizers, etc.), after which time polymerization to form thin films was simply effected by evaporation of the solvent. The dc electrical conductivity of poly(pyrrole) films formed by this method on glass slides, after rinsing the films with methanol to remove excess phosphomolybdic acid and/or monomer, was on the order of 15–30 $S\cdot cm^{-1}$ for films ranging from 40–100 nm in thickness.

Figures 1A, 1A:
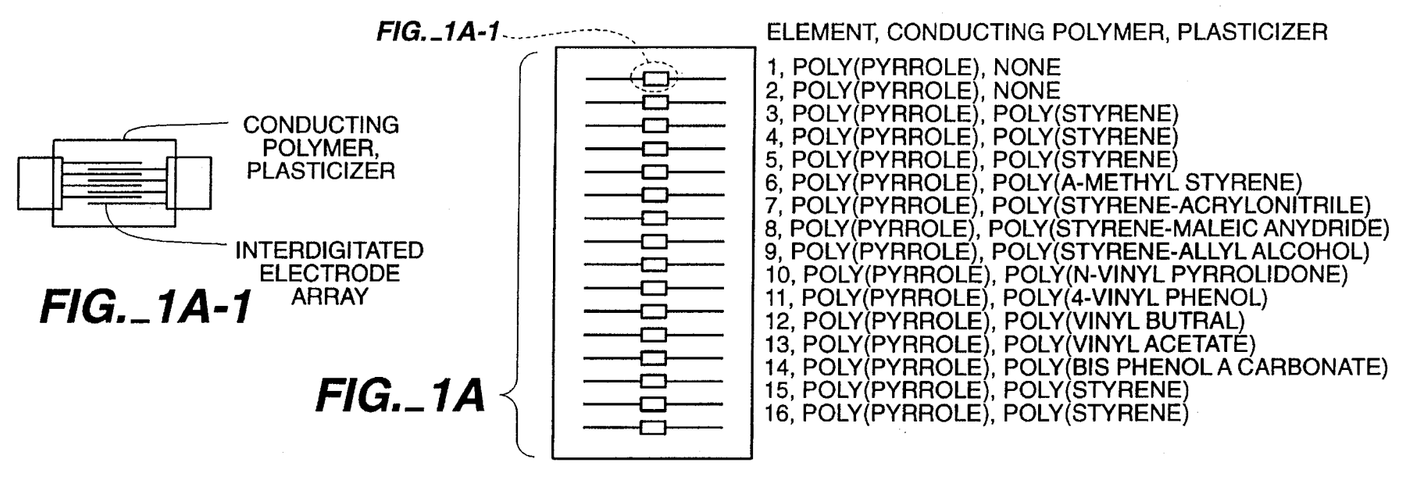
FIG. 1(A) shows an overview of sensor design.
Figure 1B:
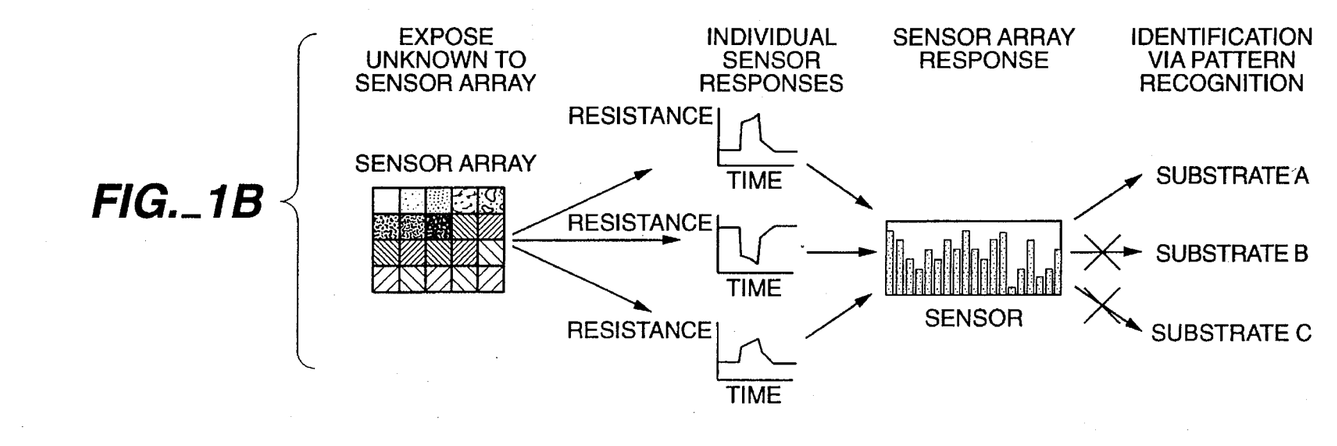
FIG. 1(B) shows an overview of sensor operation.
Figure 1C:
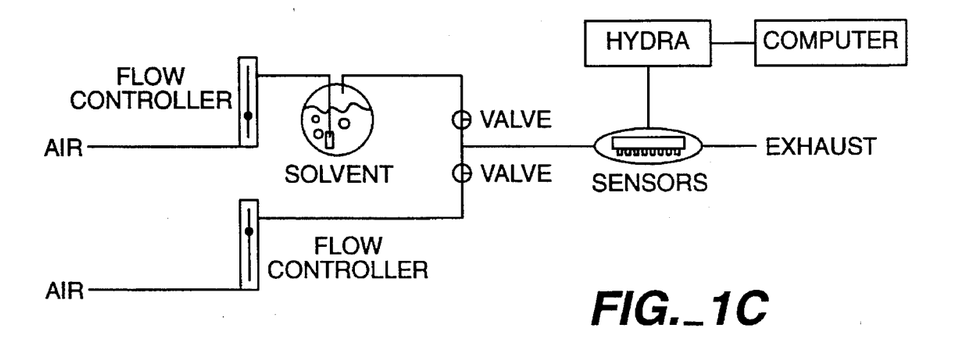
FIG. 1(C) shows an overview of system operation.
Figure 2:
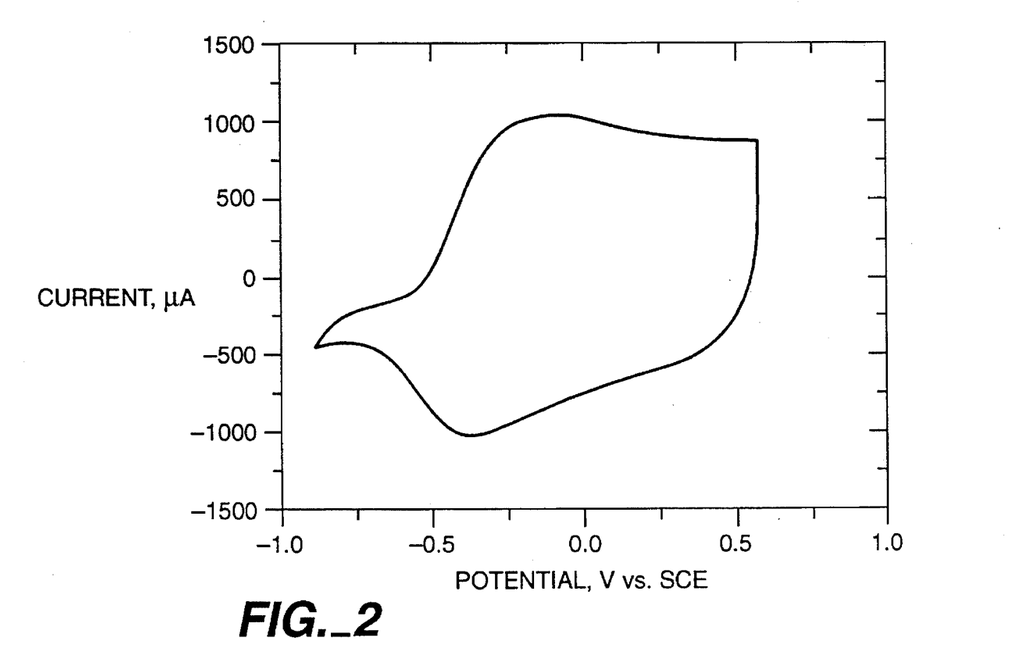
FIG. 2. Cyclic voltammogram of a poly(pyrrole)-coated platinum electrode. The electrolyte was 0.10M [(C$_4$H$_9$)$_4$N]$^+$[ClO$_4$]$^-$ in acetonitrile, with a scan rate of 0.10 V s$^{-1}$.

The poly(pyrrole) films produced in this work exhibited excellent electrochemical and optical properties. For example, FIG. 2 shows the cyclic voltammetric behavior of a chemically polymerized poly(pyrrole) film following ten cycles from −1.00 V to +0.70 V vs. SCE. The cathodic wave at −0.40 V corresponded to the reduction of poly(pyrrole) to its neutral, nonconducting state, and the anodic wave at −0.20 V corresponded to the reoxidation of poly(pyrrole) to its conducting state (reference 24). The lack of additional faradaic current, which would result from the oxidation and reduction of phosphomolybdic acid in the film, suggests that the Keggin structure of phosphomolybdic acid was not present in the film anions (reference 25) and implies that $MoO_4^{2-}$, or other anions, served as the poly(pyrrole) counterions in the polymerized films.

Figure 3A:
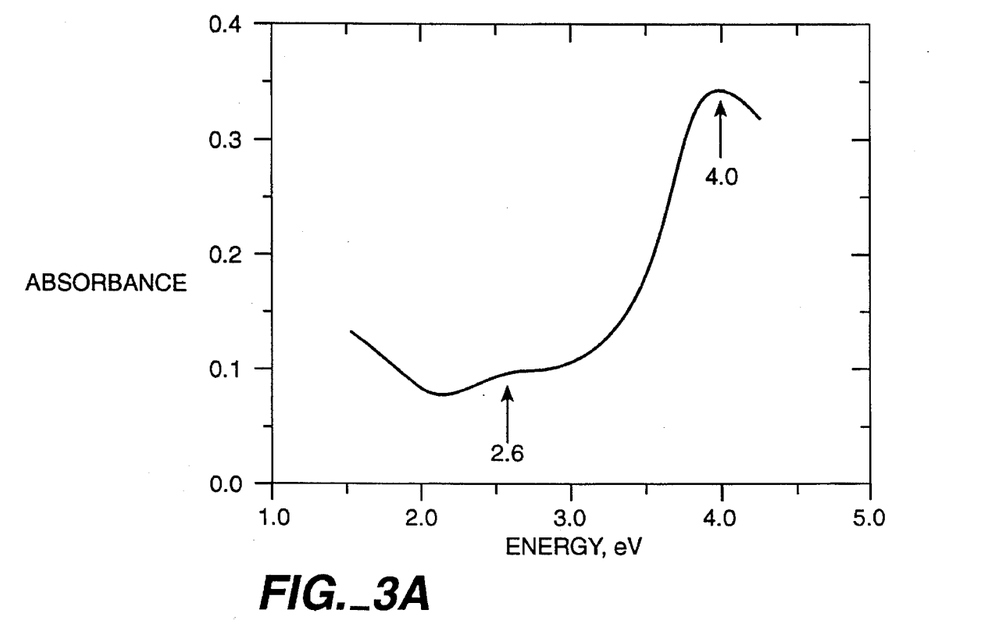
FIG. 3(A) shows the optical spectrum of a spin coated poly(pyrrole) film that had been washed with methanol to remove excess pyrrole and reduced phosphomolybdic acid.
Figure 3B:
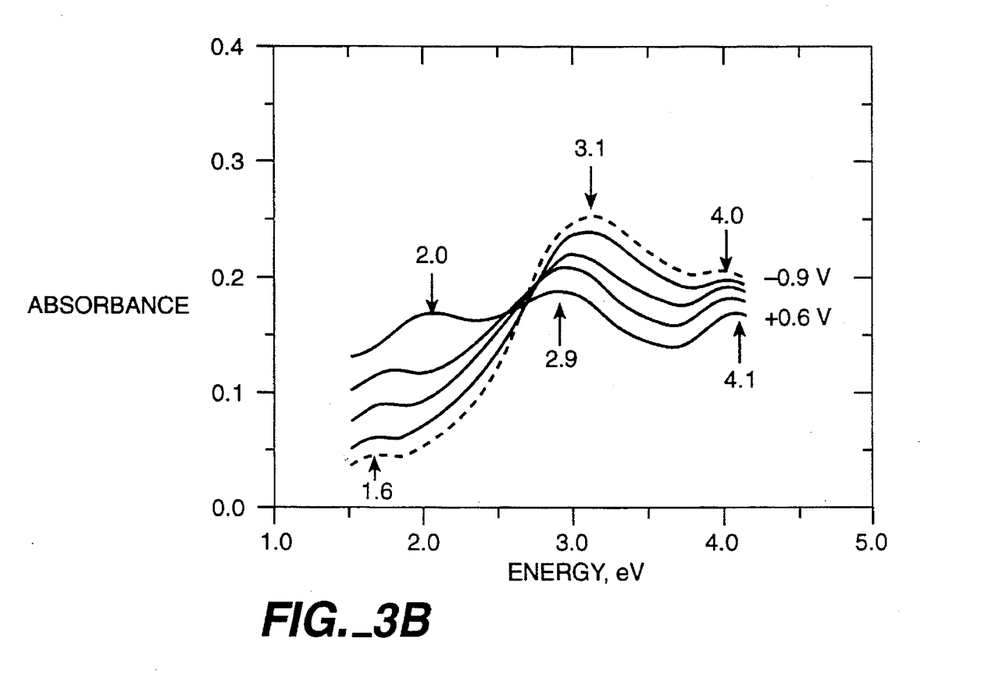
FIG. 3(B) shows the optical spectrum of a spin-coated poly(pyrrole) film on indium-tin-oxide after 10 potential cycles between +0.70 and −1.00 V vs. SCE in 0.10M [(C$_4$H$_9$)$_4$N]$^+$[ClO$_4$]$^-$ in acetonitrile at a scan rate of 0.10 V −s$^{-1}$. The spectra were obtained in 0.10M KCl–H$_2$O.

FIG. 3A shows the optical spectrum of a processed polypyrrole film that had been spin-coated on glass and then rinsed with methanol. The single absorption maximum was characteristic of a highly oxidized poly(pyrrole) (reference 26), and the absorption band at 4.0 eV was characteristic of an interband transition between the conduction and valence bands. The lack of other bands in this energy range was evidence for the presence of bipolaron states (see FIG. 3A), as have been observed in highly oxidized poly(pyrrole) (reference 26). By cycling the film in 0.10M $[(C_4H_9)_4N]^+$ $[ClO_4]^-$ acetonitrile and then recording the optical spectra in 0.10M $KCl-H_2O$, it was possible to observe optical transitions characteristic of polaron states in oxidized poly(pyrrole) (see FIG. 3B). The polaron states have been reported to produce three optical transitions (reference 26), which were observed at 2.0, 2.9, and 4.1 eV in FIG. 3B. Upon reduction of the film (c.f. FIG. 3B), an increased intensity and a blue shift in the 2.9 eV band was observed, as expected for the $\pi \to \pi^*$ transition associated with the pyrrole units contained in the polymer backbone (reference 27).

As described in the experimental section, various plasticizers were introduced into the polymer films (Table 3).

TABLE 3

Plasticizers used in array elements*

| sensor | plasticizer |
|---|---|
| 1 | none |
| 2 | none** |
| 3 | poly(styrene) |
| 4 | poly(styrene) |
| 5 | poly(styrene) |
| 6 | poly(α-methyl styrene) |
| 7 | poly(styrene-acrylonitrile) |
| 8 | poly(styrene-maleic anydride) |
| 9 | poly(styrene-allyl alcohol) |
| 10 | poly(vinyl pyrrolidone) |
| 11 | poly(vinyl phenol) |
| 12 | poly(vinyl butral) |
| 13 | poly(vinyl acetate) |
| 14 | poly(carbonate) |

*Sensors contained 2:3 (w:w) ratio of pyrrole to plasticizer.
**Film not rinsed to remove excess phosphomolybdic acid.

These inclusions allowed chemical control over the binding properties and electrical conductivity of the resulting plasticized polymers. Sensor arrays consisted of as many as 14 different elements, with each element synthesized to produce a distinct chemical composition, and thus a distinct sensor response, for its polymer film. The resistance, R, of each film-coated individual sensor was automatically recorded before, during, and after exposure to various odorants. A typical trial consisted of a 60 sec rest period in which the sensors were exposed to flowing air (3.0 liter-min$^{-1}$), a 60 sec exposure to a mixture of air (3.0 liter-min$^{-1}$) and air that had been saturated with solvent (0.5–3.5 liter-min$^{-1}$), and then a 240 sec exposure to air (3.0 liter-min$^{-1}$).

In an initial processing of the data, presented in this paper, the only information used was the maximum amplitude of the resistance change divided by the initial resistance, $\Delta R_{max}/R_i$, of each individual sensor element. Most of the sensors exhibited either increases or decreases in resistance upon exposure to different vapors, as expected from changes in the polymer properties upon exposure to different types chemicals (references 17–18). However, in some cases, sensors displayed an initial decrease followed by an increase in resistance in response to a test odor. Since the resistance of each sensor could increase and/or decrease relative to its initial value, two values of $\Delta R_{max}/R_i$ were reported for each sensor. The source of the bi-directional behavior of some sensor/odor pairs has not yet been studied in detail, but in most cases this behavior arose from the presence of water (which by itself induced rapid decreases in the film resistance) in the reagent-grade solvents used to generate the test odors of this study. The observed behavior in response to these air-exposed, water-containing test solvents was reproducible and reversible on a given sensor array, and the environment was representative of many practical odor sensing applications in which air and water would not be readily excluded.

Figure 4A:
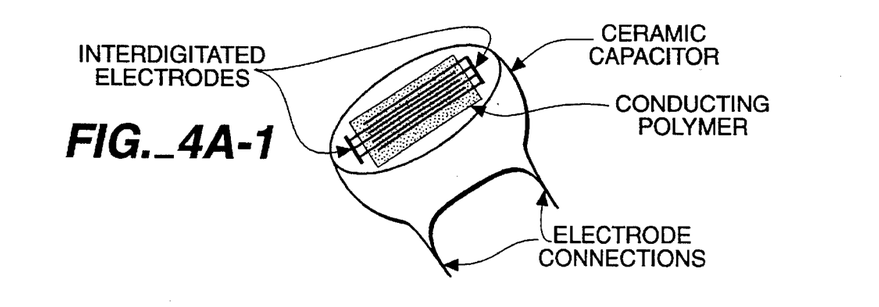
Figure 4A:
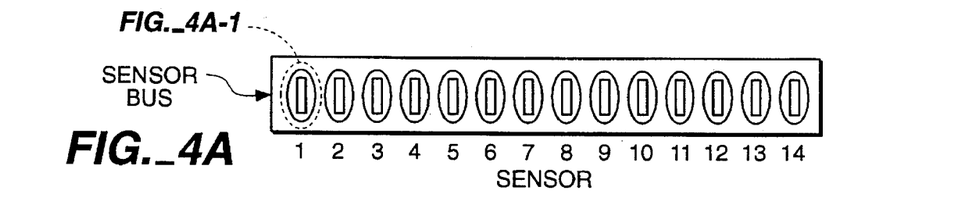
Figure 4B:
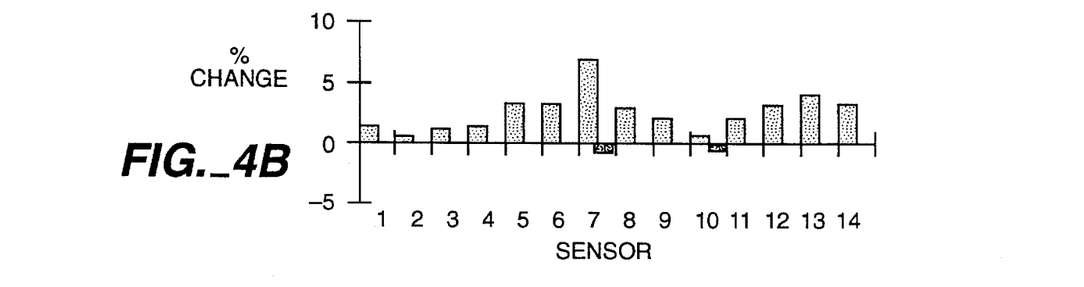
FIG. 4(B) acetone.
Figure 4C:
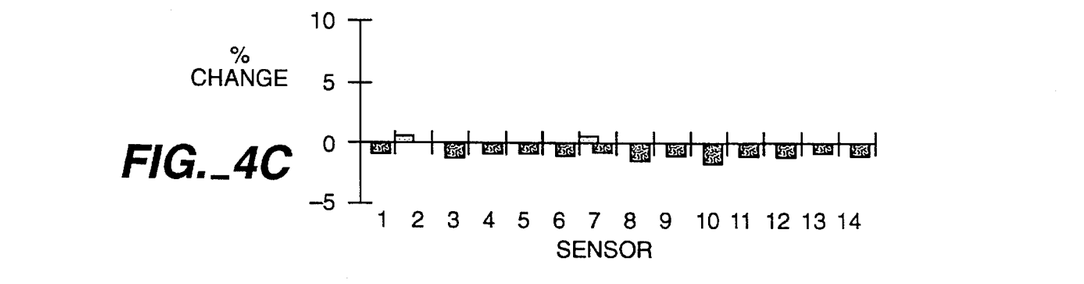
FIG. 4(C) benzene.
Figure 4D:
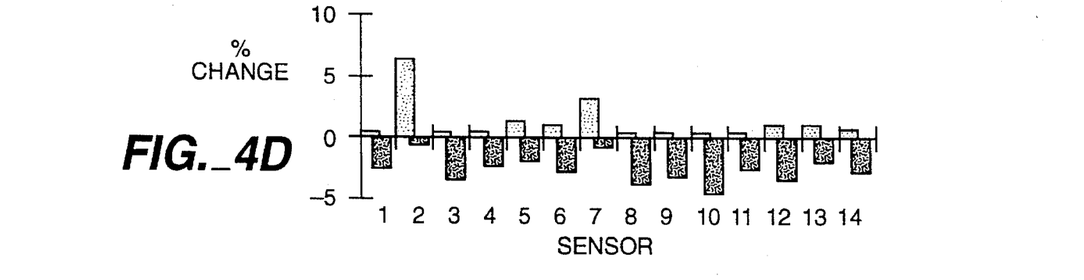
FIG. 4(D) ethanol.

FIG. 4B–D depicts representative examples of sensor amplitude responses of a sensor array (see, Table 3). In this experiment, data were recorded for 3 separate exposures to vapors of acetone, benzene, and ethanol flowing in air. The response patterns generated by the sensor array described in Table 3 are displayed for: (B) acetone; (C) benzene; and (D) ethanol. The sensor response was defined as the maximum percent increase and decrease of the resistance divided by the initial resistance (gray bar and black bar respectively) of each sensor upon exposure to solvent vapor. In many cases sensors exhibited reproducible increases and decreases in resistance. An exposure consisted of: i) a 60 sec rest period in which the sensors were exposed to flowing air (3.0 liter-min$^{-1}$); ii) a 60 sec exposure to a mixture of air (3.0 liter-min$^{-1}$) and air that had been saturated with solvent (0.5 liter-min$^{-1}$); and iii) a 240 sec exposure to air (3.0 liter-min$^{-1}$). It is readily apparent that these odorants each produced a distinctive response on the sensor array. In additional experiments, a total of 8 separate vapors (acetone, benzene, chloroform, ethanol, isopropyl alcohol, methanol, tetrahydrofuran, and ethyl acetate), chosen to span a range of chemical and physical characteristics, were evaluated over a 5 day period on a 14-element sensor array (Table 3). As discussed below, each odorant could be clearly and reproducibly identified from the others using this sensor apparatus.

Principle component analysis (reference 19) was used to simplify presentation of the data and to quantify the distinguishing abilities of individual sensors and of the array as a whole. In this approach, linear combinations of the $\Delta R_{max}/R_i$ data for the elements in the array were constructed such that the maximum variance [defined as the square of the standard deviation] was contained in the fewest mutually orthogonal dimensions. This allowed representation of most of the information contained in data sets shown in FIG. 4B–D in two (or three) dimensions. The resulting clustering, or lack thereof, of like exposure data in the new dimensional space was used as a measure of the distinguishing ability, and of the reproducibility, of the sensor array.

Figure 5:
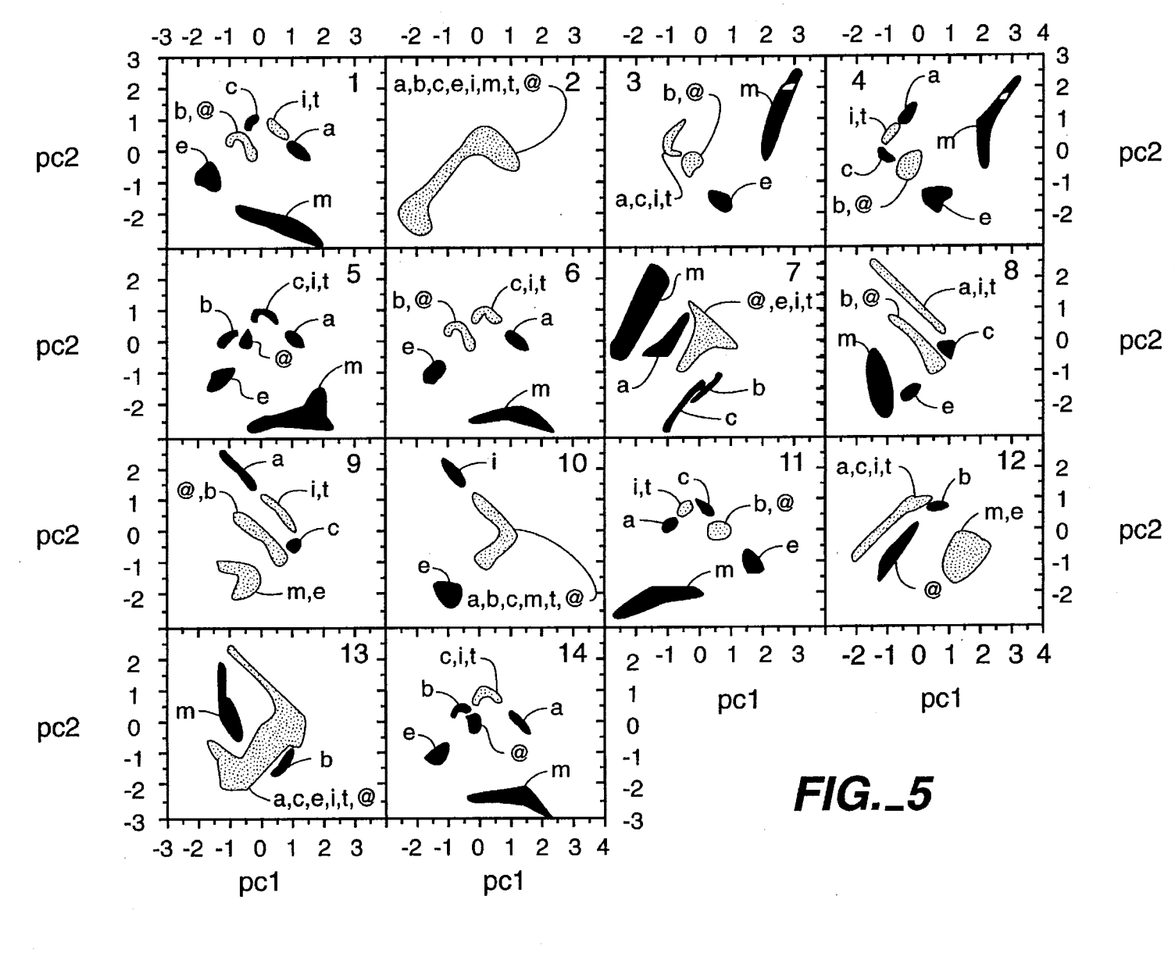
FIG. 5. Principle component analysis of autoscaled data from individual sensors containing different plasticizers. The numbers in the upper right hand corner of each square refer to the different sensor elements described in Table 3.

In order to illustrate the variation in sensor response of individual sensors that resulted from changes in the plasticizing polymer, principle component analysis was performed on the individual, isolated responses of each of the 14 individual sensor elements in a typical array (FIG. 5). Data were obtained from multiple exposures to acetone (a), benzene (b), chloroform (c), ethanol (e), isopropyl alcohol (i), methanol (m), tetrahydrofuran (+), or ethyl acetate (@) over a period of 5 days with the test vapors exposed to the array in various sequences. The numbers of the figures refer to the sensor elements described in Table 3. The units along the axes indicate the amplitude of the principle component that was used to describe the particular data set for an odor. The black regions indicate clusters corresponding to a single solvent which could be distinguished from all others; gray regions highlight dam of solvents whose signals overlapped with others around it. Exposure conditions were identical to those in FIG. 4.

Since each individual sensor produced two data values, principle component analysis of these responses resulted in only two orthogonal principal components; pc1 and pc2. As an example of the selectivity exhibited by an individual sensor element, the sensor designated as number 5 in FIG. 5 (which was plasticized with poly(styrene)) confused acetone with chloroform, isopropyl alcohol, and tetrahydrofuran. It also confused benzene with ethyl acetate, while easily distinguishing ethanol and methanol from all other solvents. Changing the plasticizer to poly (α-methyl styrene) (sensor number 6 in FIG. 5) had little effect on the spatial distribution of the responses with respect to one another and with respect to the origin. Thus, as expected, a rather slight chemical modification of the plasticizer had little effect on the relative variance of the eight test odorants. In contrast, the addition of a cyano group to the plasticizer, in the form of poly(styrene-acrylonitrile), (sensor number 7 in FIG. 5), resulted in a larger contribution to the overall variance by benzene and chloroform, while decreasing the contribution of ethanol. Changing the substituent group in the plasticizer to a hydrogen bonding acid (poly(styrene-allyl alcohol), sensor number 9 in FIG. 5) increased the contribution of acetone to the overall variance while having little effect on the other odors, with the exception of confusing methanol and ethanol. These results suggest that the behavior of the sensors can be systematically altered by varying the chemical composition of the plasticizing polymer.

Figure 6A:
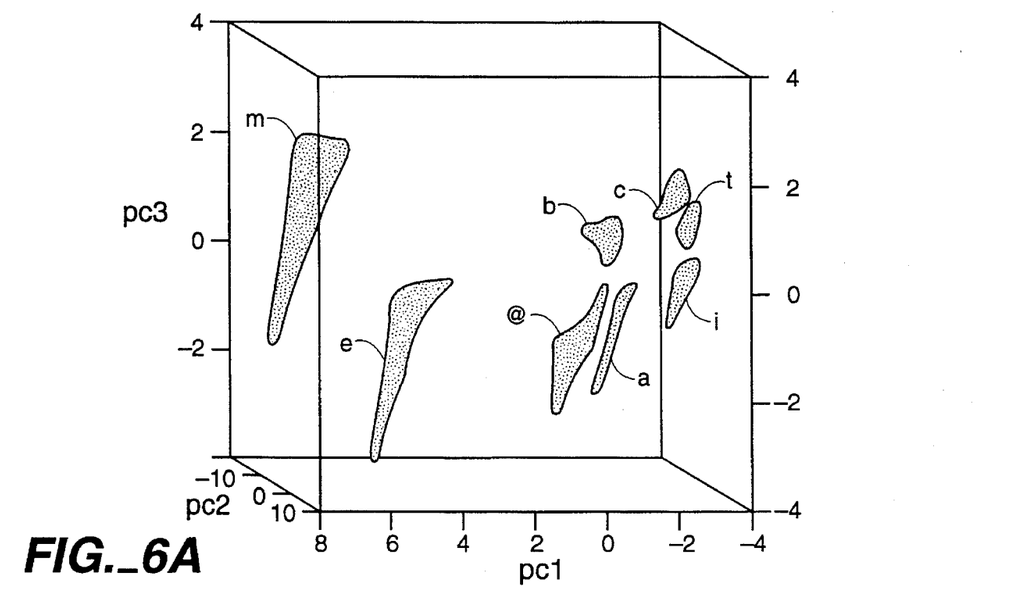
FIG. 6(A) & 6(B). Principle component analysis of data obtained from all sensors (Table 3). Conditions and symbols are identical to FIGS. 5(A)–(D).
Figure 6B:
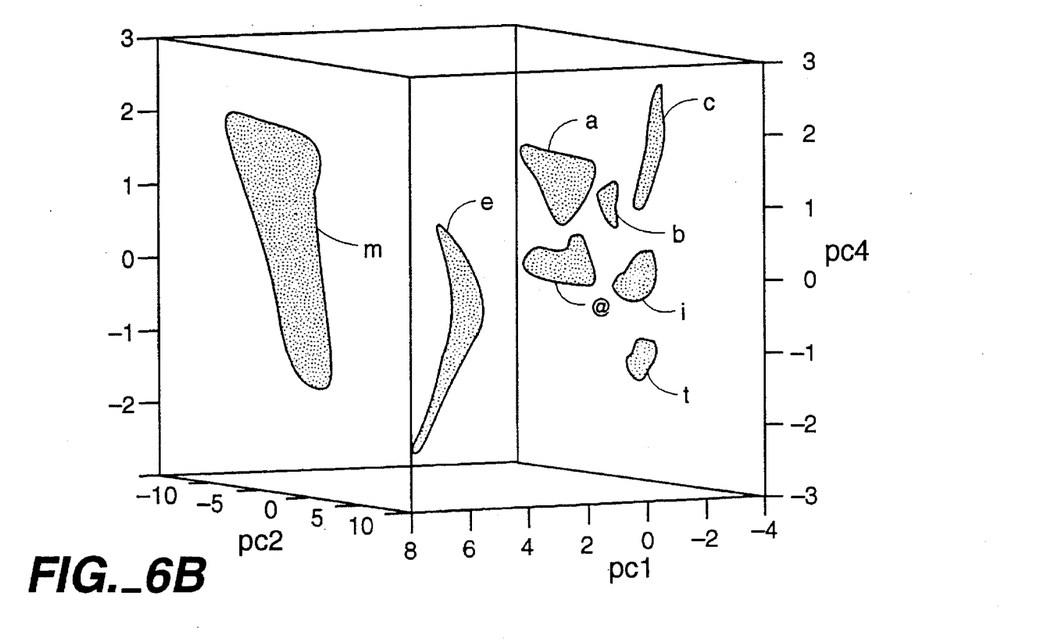

FIGS. 6A and 6B show the principle component analysis for all 14 sensors described in Table 3 and FIGS. 4 and 5. When the solvents were projected into a three dimensional odor space (FIG. 6A or 6B), all eight solvents were easily distinguished with the specific array discussed herein. Detection of an individual test odor, based only on the criterion of observing ~1% $\Delta R_{max}/R_i$ values for all elements in the array, was readily accomplished at the parts per thousand level with no control over the temperature or humidity of the flowing air. Further increases in sensitivity are likely after a thorough utilization of the temporal components of the $\Delta R_{max}/R_i$ data as well as a more complete characterization of the noise in the array.

Figure 7A:
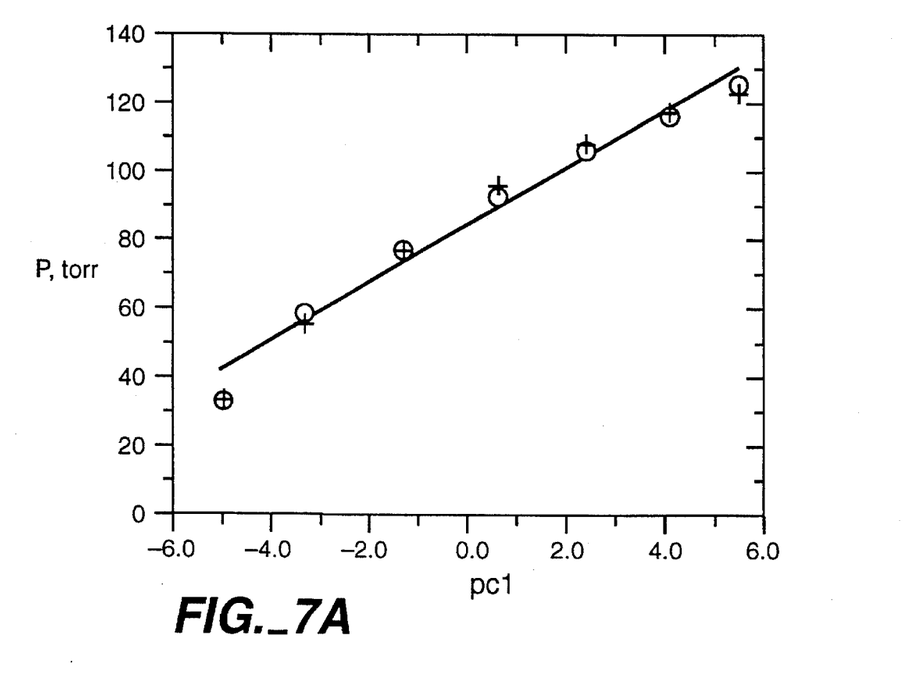
FIG. 7(A). Plot of acetone partial pressure (O) as a function of the first principle component; linear least square fit (–) between the partial pressure of acetone and the first principle component ($P_a$=8.26.pc1+83.4, $R^2$=0.989); acetone partial pressure (+) predicted from a multi-linear least square fit between the partial pressure of acetone and the first three principle components ($P_a$=8.26.pc1–0.673.pc2+6.25.pc3+83.4, $R^2$=0.998).

We have also investigated the suitability of this sensor array for identifying the components of certain test mixtures. This task is greatly simplified if the array exhibits a predictable signal response as the concentration of a given odorant is varied, and if the responses of various individual odors are additive (i.e. if superposition is maintained). When a 19-element sensor array was exposed to a number, n, of different acetone concentrations in air, the $(CH_3)_2CO$ concentration was semi-quantitavely predicted from the first principle component. This was evident from a good linear least square fit through the first three principle components see FIG. 7A for the linear least square fit for the first principle component.

Figure 7B:
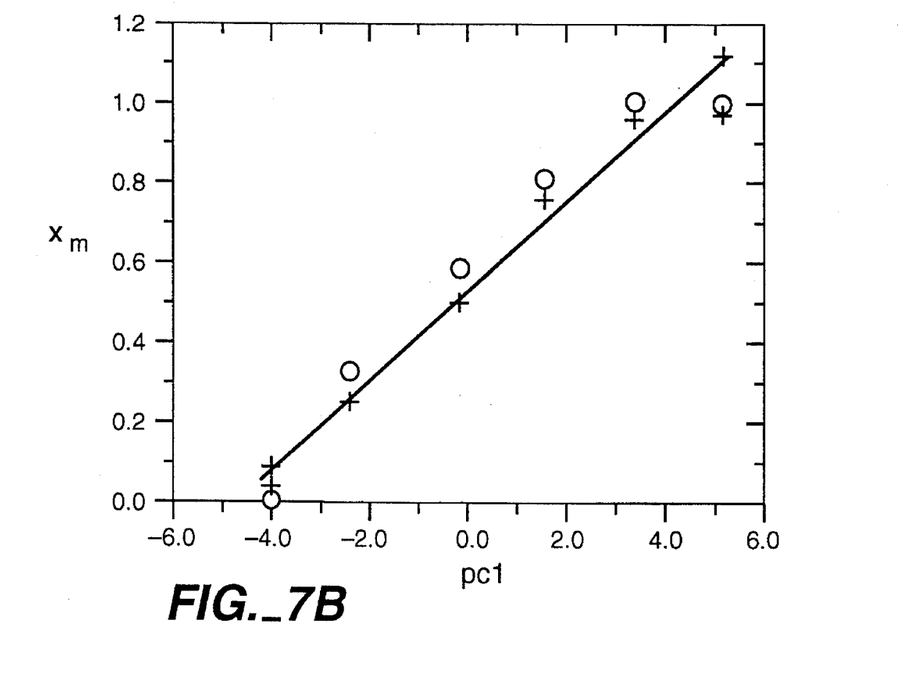
FIG. 7(B). Plot of the mole fraction of methanol, $x_m$, (O) in a methanol—ethanol mixture as a function of the first principle component; linear least square fit (–) between $x_m$ and the first principle component ($x_m$=0.112.pc1+0.524, $R^2$=0.979); $x_m$ predicted from a multi-linear least square fit (+) between $x_m$ and the first three principle components ($x_m$=0.112.pc1–0.0300.pc2–0.0444.pc3+0.524, $R^2$=0.987).

The same sensor array was also able to resolve the components in various test methanol-ethanol mixtures (reference 29). As shown in FIG. 7B, a linear relationship was observed between the first principle component and the mole fraction of methanol in the liquid phase, $x_m$, in a $CH_3OH$-$C_2H_5OH$ mixture, demonstrating that superposition held for this mixture/sensor array combination. Furthermore, although the components in the mixture could be predicted fairly accurately from just the first principle component, an increase in the accuracy could be achieved using a multi-linear least square fit through the first three principle components. This relationship held for $CH_3OH/(CH_3OH+C_2H_5OH)$ ratios of 0 to 1.0 in air-saturated solutions of this vapor mixture. The conducting polymer-based sensor arrays could therefore not only distinguish between pure test vapors, but also allowed analysis of concentrations of odorants as well as analysis of binary mixtures of vapors.

In summary, the results presented herein advance the area of analyte sensor design. A relatively simple array design, using only a multiplexer low-power dc electrical resistance readout signal, has been shown to readily distinguish between various test odorants. Such conducting polymer-based arrays are simple to construct and modify, and afford an opportunity to effect chemical control over the response pattern of a vapor. For example, by increasing the ratio of plasticizer to conducting polymer, it is possible to approach the percolation threshold, at which point the conductivity exhibits a very sensitive response to the presence of the sorbed molecules. Furthermore, producing thinner films will afford the opportunity to obtain decreased response times, and increasing the number of plasticizing polymers and polymer backbone motifs will likely result in increased diversity among sensors. This type of polymer-based array is chemically flexible, is simple to fabricate, modify, and analyze, and utilizes a low power dc resistance readout signal transduction path to convert chemical data into electrical signals. It provides a new approach to broadly-responsive odor sensors for fundamental and applied investigations of chemical mimics for the mammalian sense of smell. Such systems are useful for evaluating the generality of neural network algorithms developed to understand how the mammalian olfactory system identifies the directionality, concentration, and identity of various odors.

Fabrication and Testing of Carbon Black-based Sensor Arrays.

Sensor Fabrication. Individual sensor elements were fabricated in the following manner. Each non-conductive polymer (80 mg, see Table 4) was dissolved in 6 ml of THF.

TABLE 4

| Sensor # | Non-Conductive Polymer |
|---|---|
| 1 | poly(4-vinyl phenol) |
| 2 | poly(styrene - allyl alcohol) |
| 3 | poly(α-methyl styrene) |
| 4 | poly(vinyl chloride - vinyl acetate) |
| 5 | poly(vinyl acetate) |
| 6 | poly(N-vinyl pyrrolidone) |
| 7 | poly(bisphenol A carbonate) |
| 8 | poly(styrene) |
| 9 | poly(styrene-maleic anhydride) |
| 10 | poly(sulfone) |

Then, 20 mg of carbon black (BP 2000, Cabot Corp.) were suspended with vigorous mixing. Interdigitated electrodes (the cleaved capacitors previously described) were then dipped into this mixture and the solvent allowed to evaporate. A series of such sensor elements with differing non-conductive polymers were fabricated and incorporated into a commercial bus strip which allowed the chemiresistors to be easily monitored with a multiplexing ohmmeter.

Figure 8:
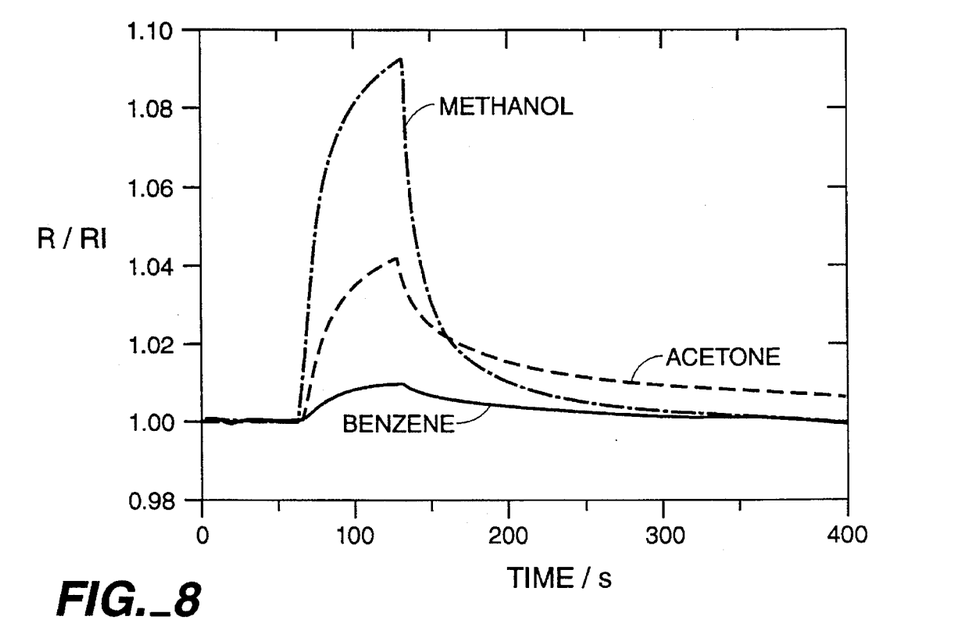
FIG. 8. The resistance response of a poly(N-vinylpyrrolidone):carbon black (20 w/w % carbon black) sensor dement to methanol, acetone, and benzene. The analyte was introduced at t=60 s for 60 s. Each trace is normalized by the resisance of the sensor element (approx. 125 Ω) before each exposure.
Figure 9:
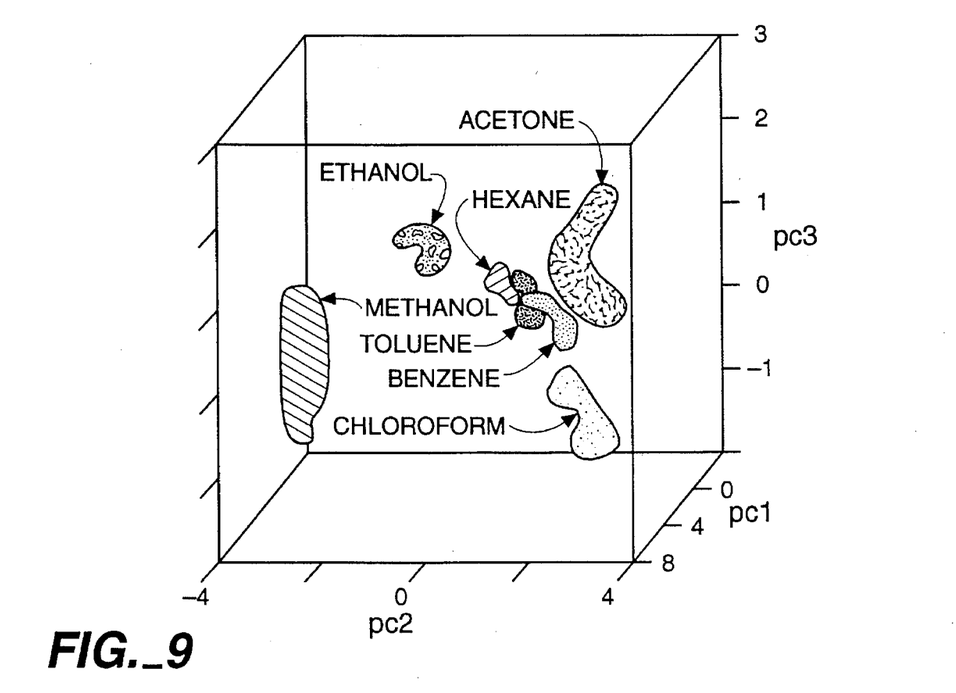
FIG. 9. First three principal components for the response of a carbon-black based sensor array with 10 element. The non-conductive components of the carbon-black composites used are listed in Table 3, and the resistors were 20 w/w % carbon black.

Sensor Array Testing. To evaluate the performance of the carbon-black based sensors, arrays with as many as twenty elements were exposed to a series of analytes. A sensor exposure consisted of (1) a sixty second exposure to flowing air (6 liter min−1), (2) a sixty second exposure to a mixture of air (6 liter min−1) and air that had been saturated with the analyte (0.5 liter min−1), (3) a five minute recovery period during which the sensor array was exposed to flowing air (6 liter min−1). The resistance of the elements were monitored during exposure, and depending on the thickness and chemical make-up of the film, resistance changes as large as 250% could be observed in response to an analyte. In one experiment, a 10 element sensor array consisting carbon-black composites formed with a series of non-conductive polymers (see Table 4) was exposed to acetone, benzene, chloroform, ethanol, hexane, methanol, and toluene over a two day period. A total of 58 exposures to these analytes were performed in this time period. In all cases, resistance changes in response to the analytes were positive, and with the exception of acetone, reversible (see FIG. 8). The maximum positive deviations were then subjected to principal component analysis in a manner analogous to that described for the poly(pyrrole) based sensor. FIG. 9 shows the results of the principal component analysis for the entire 10-element array. With the exception of overlap between toluene with benzene, the analytes were distinguished from one and other.

Cited References: 1. Lundström et al. (1991) *Nature* 352:47–50; 2. Shurmer and Gardner (1992) *Sens. Act.* B 8:1–11; 3. Reed (1992) *Neuron* 8:205–209; 4. Lancet and Ben-Airie (1993) *Curr. Biol.* 3:668–674; 5. Kauer (1991) *TINS* 14:79–85; 6. DeVries and Baylor (1993) *Cell* 10(S):139–149; 7. Gardner et al. (1991) *Sens. Act.* B 4:117–121; 8. Gardner et al. (1991) *Sens. Act.* B 6:71–75; 9. Corcoran et al. (1993) *Sens. Act.* B 15:32–37; 10. Grate and Abraham (1991) *Sens. Act.* B 3:85–111; 11. Grate et al. (1993) *Anal. Chem.* 65:1868–1881; 12. Stetter et al. (1986) *Anal. Chem.* 58:860–866; 13. Stetter et al. (1990) *Sens. Act.* B 1:43–47; 14. Stetter et al. (1993) *Anal. Chem. Acta* 284:1–11; 15. Pearce et al. (1993) *Analyst* 118:371–377; 16. Shurmer et al. (1991) *Sens. Act.* B 4:29–33; 17. Topart and Josowicz (1992) *J. Phys. Chem.* 96:7824–7830; 18. Charlesworth et al. (1993) *J. Phys. Chem.* 97:5418–5423; 19. Hecht (1990) *Mathematics in Chemistry: An Introduction to Modern Methods* (Prentice Hall, Englewood Cliffs, N.J.); 20. Pope (1983) *Heteropoly and Isopoly Oxometalates* (Springer-Verlag, New York), chap. 4; 21. Salmon et al. (1982) *J. Polym. Sci., Polym. Lett.* 20:187–193; 22. Andrieux et al. (1990) *J. Am. Chem. Soc.* 112:2439–2440; 23. Diaz et al. (1981) *J. Electroanal. Chem.* 121:355–361; 24. Kanazawa et al. (1981) *Synth. Met.* 4:119–130; 25. Bidan et al. (1988) *J. Electroanal. Chem.* 251:297–306; 26. Kaufman et al. (1984) *Phys. Rev. Lett.* 53:1005–1008; 27. Yakushi et al. (1983) *J. Chem. Phys.* 79:4774–4778; and 28. Morris et al. (1942) *Can. J. Res.* B 20:207–211.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A sensor array for detecting an analyte in a fluid comprising at least first and second chemically sensitive resistors electrically connected to an electrical measuring apparatus, each of said chemically sensitive resistors comprising:

a mixture of nonconductive organic polymer and a conductive material compositionally different than said nonconductive organic polymer, wherein each resistor provides an electrical path through said mixture of nonconductive organic polymer and said conductive material, a first electrical resistance when contacted with a first fluid comprising a chemical analyte at a first concentration, and a second electrical resistance when contacted with a second fluid comprising said chemical analyte at a second different concentration, wherein the difference between the first electrical resistance and the second electrical resistance of said first chemically sensitive resistor being different from the difference between the first electrical resistance and the second electrical resistance of said the second chemically sensitive resistor under the same conditions.

2. A sensor array according to claim 1, wherein said nonconductive organic polymer of said first chemically sensitive resistor is different from said nonconductive organic polymer of said second chemically sensitive resistor.

3. A sensor array according to claim 1, wherein said conductive material is an inorganic conductor.

4. A system for detecting an analyte in a fluid, said system comprising:

a sensor array comprising at least first and second chemically sensitive resistors, each chemically sensitive resistor comprising a mixture of nonconductive organic polymer and conductive material compositionally different than said nonconductive organic polymer, each resistor providing an electrical path through said mixture of nonconductive organic polymer and said conductive material, a first electrical resistance when contacted with a first fluid comprising a chemical analyte at a first concentration and a second different electrical resistance when contacted with a second fluid comprising said chemical analyte at a second different concentration, wherein the difference between the first electrical resistance and the second electrical resistance of said first chemically sensitive resistor being different from the difference between the first electrical resistance and the second electrical resistance of said second chemically sensitive resistor under the same conditions;

an electrical measuring device electrically connected to said sensor array; and a computer comprising a resident algorithm;

said electrical measuring device detecting said first and said second electrical resistances in each of said chemically sensitive resistors and said computer assembling said resistances into a sensor array response profile.

5. A system according to claim 4, wherein said nonconductive organic polymer of said first chemically sensitive resistor is different from said nonconductive organic polymer of said second chemically sensitive resistor.

6. A system according to claim 4, wherein said conductive material is an inorganic conductor.

7. A method for detecting the presence of an analyte in a fluid, said method comprising:

resistively sensing the presence of an analyte in a fluid with a sensor array comprising at least first and second chemically sensitive resistors each comprising a mixture of nonconductive organic polymer and a conductive material compositionally different than said nonconductive organic polymer, each resistor providing an electrical path through said mixture of nonconductive organic polymer and said conductive material, a first electrical resistance when contacted with a first fluid comprising a chemical analyte at a first concentration and a second different electrical resistance when contacted with a second fluid comprising said chemical analyte at a second different concentration.

8. A method according to claim 7, wherein said nonconductive organic polymer of said first chemically sensitive resistor is different from said nonconductive organic polymer of said second chemically sensitive resistor.

9. A method according to claim 7, wherein said conductive material is an inorganic conductor.

10. A method according to claim 7, said first and said second resistance each being a resistance over time.

* * * * *

UNITED STATES PATENT AND TRADEMARK OFFICE
CERTIFICATE OF CORRECTION

PATENT NO. : 5,571,401

DATED : November 5, 1996

INVENTOR(S) : LEWIS et al.

It is certified that error appears in the above-indentified patent and that said Letters Patent is hereby corrected as shown below:

Column 1, line 6, immediately following "(CHE 9202583)" insert --and ARPA (ONR Grant No. N00014-89-J-3198)--.

Signed and Sealed this

Eighth Day of December, 1998

Attest:

BRUCE LEHMAN

Attesting Officer

Commissioner of Patents and Trademarks